US00PP16276P3

(12) United States Plant Patent
Noack

(10) Patent No.: US PP16,276 P3
(45) Date of Patent: Feb. 21, 2006

(54) SHRUB ROSE PLANT NAMED 'NOA250092'

(50) Latin Name: *Rosa hybrida*
Varietal Denomination: NOA250092

(76) Inventor: Reinhard Noack, Im Fenne 54, Gütersloh (DE), 33334

( * ) Notice: Subject to any disclaimer, the term of this patent is extended or adjusted under 35 U.S.C. 154(b) by 144 days.

(21) Appl. No.: 10/781,605

(22) Filed: Feb. 18, 2004

(65) Prior Publication Data

US 2005/0183177 P1 Aug. 18, 2005

(51) Int. Cl.
*A01H 5/00* (2006.01)

(52) U.S. Cl. ..... Plt./107
(58) Field of Classification Search ..... Plt./107
See application file for complete search history.

*Primary Examiner*—Anne Marie Grunberg
*Assistant Examiner*—Annette H Para
(74) *Attorney, Agent, or Firm*—RatnerPrestia

(57) ABSTRACT

A new and distinct variety of rose plant of the shrub class particularly well suited for growing as an attractive ornamentation to the landscape is disclosed. The plant is characterized by its numerous, attractive soft pink blossoms, whose attractive appearance is retained on aging; its bright orange stamens, which contrast attractively with soft pink of the petals; its upright, dense, and compact growth habit; its attractive dark green foliage; and its excellent disease resistance.

2 Drawing Sheets

FIELD OF THE INVENTION

This invention relates to a new and distinct variety of rose plant of the shrub rose class.

SUMMARY OF THE INVENTION

The present invention relates to a new and distinct variety of rose plant of the shrub class, which is particularly well suited for growing as an attractive ornamentation to the landscape. The varietal denomination of this new and distinct variety of rose plant is 'NOA250092'.

By cross pollination of a Noack Rosen Seedling (unpatented in the United States), which has soft pink single blooms, with the variety known as 'Blühendes Barock' (variety: NOAbell) (Noack Rosen, 1997, unpatented in the United States), a floribunda rose with medium pink blooms, I have produced a new and improved rose variety which is distinguished from all other rose varieties of which I am aware, as evidenced by the following unique combination of characteristics which are outstanding therein:

(1) its numerous, attractive soft pink blossoms, whose attractive appearance is retained on aging;

(2) its bright orange stamens, which contrast attractively with soft pink of the petals;

(3) its upright, dense, and compact growth habit;

(4) its attractive dark green foliage; and (5) its excellent disease resistance.

Asexual reproduction of this new variety was first performed in Gütersloh, Germany. Asexual reproduction of this new variety by budding and by cuttings shows that the foregoing and all other characteristics come true to form and are established and transmitted through succeeding propagations.

BRIEF DESCRIPTION OF THE ILLUSTRATIONS

The accompanying illustrations show typical specimens of the vegetative growth and flowers of this new variety in different stages of development, depicted in color as nearly true as it is reasonably possible to make the same in a color illustration of this character.

FIG. 1 shows typical flowers of this new variety, in which the bright orange stamens and pollen contrasts attractively with soft pink of the petals.

FIG. 2 shows typical buds, leaves and flowers of this new variety.

DETAILED DESCRIPTION OF THE NEW VARIETY

The following is a detailed description of my new rose cultivar with color descriptions using terminology in accordance with a Royal Horticulture Society Colour Chart (R.H.S.C.C.), except where ordinary dictionary significance of color is indicated.

Genus and species: *Rosa hybrida.*
Varietal denomination: 'NOA250092'.
Parentage:
*Seed parent.*—'NOACK ROSEN Seedling' (unpatented in the United States).
*Pollen patent.*—'NOACK ROSEN Blühendes Barock' (variety: NOAbell) (unpatented in the United States).

The new rose plant can be distinguished from its parents by its flowers. The seed parent has single flowers, with 5 to 8 petals. The new rose variety has semi-double flowers, with about 16 soft pink petals, which contrast attractively with the bright orange stamens. The pollen parent has medium pink, double flowers. In addition, the pollen parent has a small and compact growth habit. No similar cultivars are known.

Class: Shrub.

The following observations were made on one and half-year-old budded specimens grown outdoors in Gütersloh, Germany, during the month of July 2002.

FLOWER

Blooming habit: Recurring, continuous.
Time of beginning of flowering: Medium to late.

A. Bud:
*Size.*—Typically about 2 cm in length when the petals start to unfurl.
*Form.*—Long and pointed.
*Sepals.*—Five. There are three normally appendaged sepals. There are two unappendaged sepals. Length — about 1 cm. Width — about 0.5 cm. Shape — triangular, pointed. Base shape — cuneate. Apex shape — aristate. Surface Texture — smooth. Color — Upper side — Green. Green Group 138A. Underside — Green. Green Group 136C.
*Color.*—Soft pink, near Red Group 49D when sepals start to unfurl.
*Peduncle.*—Length — 5–6 cm. Aspect — straight and smooth. Color — Green. Green Group 144B.
*Calyx tube.*—Color — Green Group 144A.

B. Bloom:
*Size.*—Average fully open size about 5 cm across.
*Borne.*—In numerous sprays, typically 5 to 11 blooms per spray.
*Form.*—Initially cup-shaped, flattening on maturity.
*Fragrance.*—Weak.

C. Petals:
*Size.*—About 2.5 to 3 cm long. About 2.5 cm wide.
*Shape.*—Deltoid.
*Texture.*—Smooth on both upper side and lower side.
*Arrangement.*—In a generally regular pattern with overlapping edges.
*Number.*—Semi-double. About 16 petals.
*Color.*—Soft pink, both the upper side and the under side near Red Group 49C. At base of inner side: White, near 157D. At base of outer side: White, near 155A to 155C.
*Color change.*—Upper side may become colored with bright orange pollen, which attractively contrasts with soft pink of the petal. Color of the upper side changes to Red Group 49D just before the petals drop off. Color of the under side changes to Red Group 56D just before the petals drop off.
*Petal drop.*—Good with clean disengagement of the petals.
*Lasting quality.*—Very good. Attractive appearance is retained on aging.

REPRODUCTIVE PARTS

A. Stamen, anthers, filaments: Stamens arranged regularly around the style. The pollen causes the anthers to appear bright orange. Orange Group 25C.
B. Pollen: Abundant. Color: bright orange. Orange Group 25C.
C. Styles, stigmas, and pistils: Arrangement — regular. Orange Group 25C. Up to about 80 per bloom.
D. Hips: Few. Small to medium, pear-shaped, about 1.5 cm in length. Changing from green to red on ripening.
E. Seeds: Few.

PLANT

A. Form: Young plants exhibit an upright growth habit, spreading to form a compact bush with dense foliage as the plant matures.
B. Growth: Vigorous. Height obtained in first season — about 60–80 cm. Mature Plant: Height — about 80–100 cm. Width — about 60–80 cm.
C. Foliage: Compound, odd-pinnate, typically 5 leaflets per leaf.
*Size.*—Leaflets — about 3 cm to 6 cm long and about 2 cm to 4 cm wide.
*Quantity.*—Abundant, covers plant to ground.
*Arrangement.*—Alternate: uniform and equally spaced.
*Color.*—Old foliage — Upper side — near Green Group 132B, under side — near Green Group 129B.
*Shape.*—Oval, pointed at tip.
*Venation.*—Non-parallel.
*Texture.*—Leathery. Upper side — smooth, glossy. Under side — matte.
*Edge.*—Slightly serrated, ordinary.
*Serration.*—Very small and uniform.
*Petiole/rachis.*—Color: Upper side — near Green Group 132B. Length — about 1 cm. Surface Texture — smooth.
*Stipules.*—Old foliage — Upper side — near Green Group 132B. Length — about 0.8 to 1.2 cm. Width at top — about 0.5 cm.
*Resistance to disease.*—Blackspot — excellent. Powdery Mildew — excellent Rust — excellent.

D. Wood:
*New wood.*—Color — green. Bark — smooth.
*Old wood.*—Color — darker green than new wood. Bark — smooth.

E. Prickles:
*Short prickles.*—Few.
*Long prickles.*—Quantity — ordinary. Size — medium, about 4.5 mm long. Shape — pointed and slightly curved down. Form — concave. Position — irregular. Color: — initially light red-brown changing to dark brown at maturity.

F. Winter hardiness: Good.

I claim:

1. A new and distinct variety of rose plant of the shrub class which is particularly well suited for growing as an attractive ornamentation to the landscape, substantially as herein shown and described, characterized particularly as to novelty by its numerous, attractive soft pink blossoms, whose attractive appearance is retained on aging; its bright orange stamens, which contrast attractively with soft pink of the petals; its upright, dense, and compact growth habit; its attractive dark green foliage; and its excellent disease resistance.

* * * * *

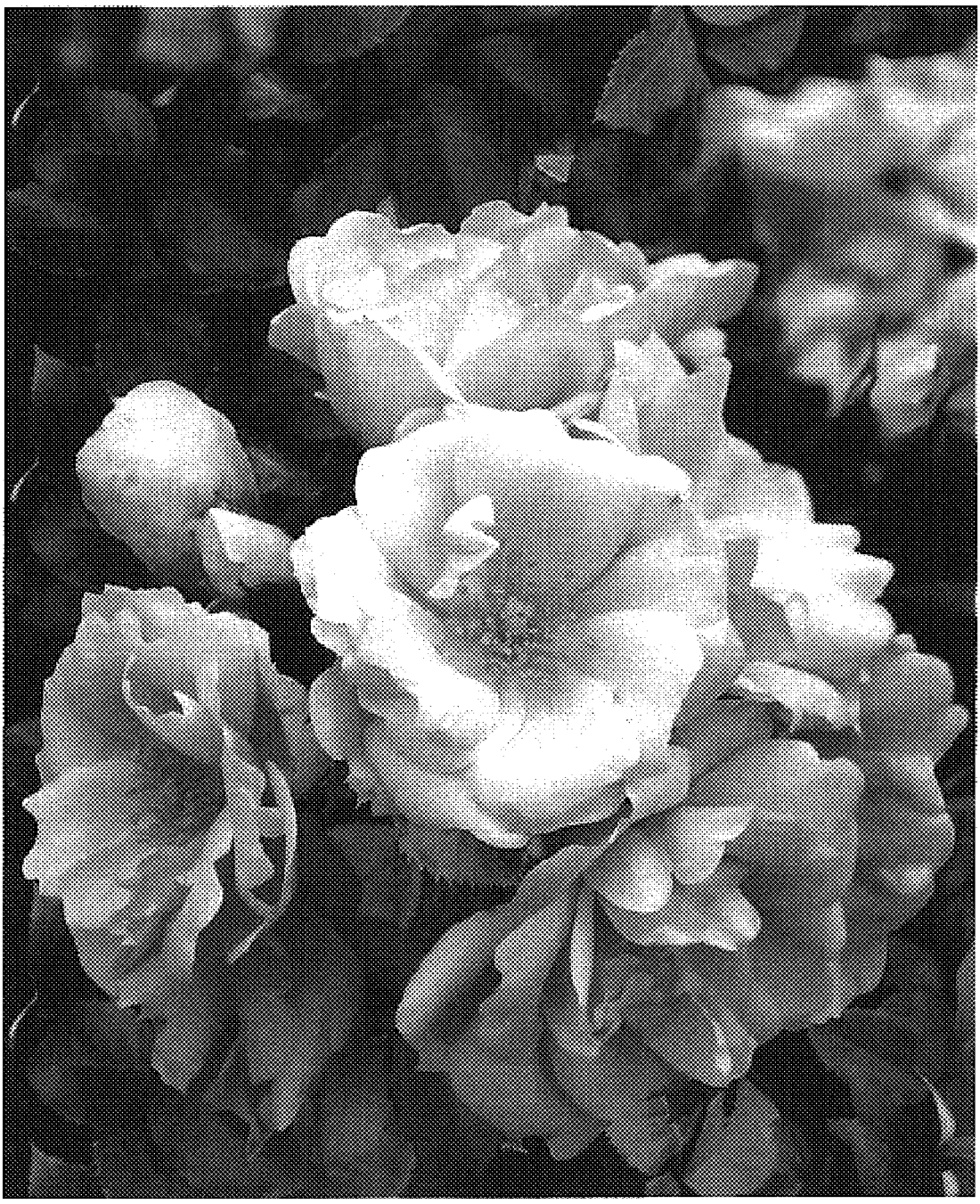

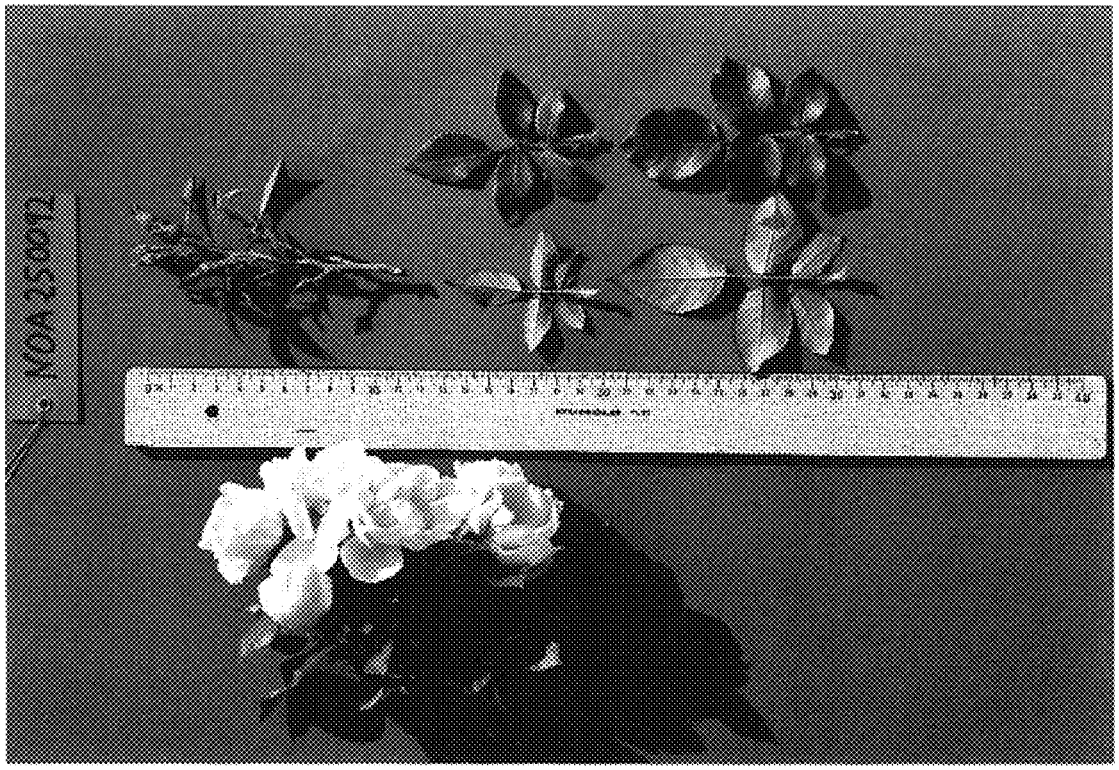
NOA 2SCOT2